United States Patent
Piro

(10) Patent No.: US 10,945,893 B1
(45) Date of Patent: Mar. 16, 2021

(54) SURGICAL SPONGE LOCATOR SYSTEM

(71) Applicant: Peter Piro, Milledgeville, GA (US)

(72) Inventor: Peter Piro, Milledgeville, GA (US)

(*) Notice: Subject to any disclaimer, the term of this patent is extended or adjusted under 35 U.S.C. 154(b) by 0 days.

(21) Appl. No.: 17/032,075

(22) Filed: Sep. 25, 2020

(51) Int. Cl.
| A61F 13/44 | (2006.01) |
| A61B 90/98 | (2016.01) |
| A61B 50/37 | (2016.01) |
| A61F 13/14 | (2006.01) |
| A61B 90/00 | (2016.01) |
| A61B 5/00 | (2006.01) |
| A61B 7/00 | (2006.01) |

(52) U.S. Cl.
CPC .............. *A61F 13/44* (2013.01); *A61B 50/37* (2016.02); *A61B 90/98* (2016.02); *A61F 13/14* (2013.01); *A61B 5/0059* (2013.01); *A61B 7/00* (2013.01); *A61B 90/39* (2016.02); *A61B 2050/375* (2016.02); *A61B 2090/0805* (2016.02); *A61B 2090/3945* (2016.02); *A61B 2090/3995* (2016.02)

(58) Field of Classification Search
CPC .......... A61F 13/44; A61F 13/14; A61B 50/37; A61B 90/98; A61B 2090/0805; A61B 2050/375; A61B 2090/3945; A61B 90/39; A61B 7/00; A61B 5/0059; A61B 2090/3995
See application file for complete search history.

(56) References Cited

U.S. PATENT DOCUMENTS

| 4,658,818 A | 4/1987 | Miller, Jr. |
| 5,190,059 A | 3/1993 | Fabian |
| 5,650,596 A * | 7/1997 | Morris .................. A61B 50/37 177/25.13 |
| 7,784,468 B2 | 8/2010 | Fabian |
| 9,168,104 B2 | 10/2015 | Dein |
| 2004/0129279 A1* | 7/2004 | Fabian .................. A61F 13/44 128/899 |
| 2005/0049564 A1* | 3/2005 | Fabian .................. A61F 13/36 604/362 |
| 2008/0200926 A1* | 8/2008 | Verard .................. A61B 90/98 606/130 |
| 2009/0012418 A1 | 1/2009 | Gerlach |
| 2014/0303606 A1* | 10/2014 | Garner-Richards ........ A61B 17/06114 606/1 |
| 2015/0216610 A1* | 8/2015 | Augustine ............. A61B 90/98 235/385 |

FOREIGN PATENT DOCUMENTS

WO    WO2013041976    3/2013

* cited by examiner

*Primary Examiner* — Thien T Mai

(57) ABSTRACT

A surgical sponge locator system for locating sponges after surgery for removal includes a base having a sponge portion and a housing portion. A plurality of surgical sponges is coupled within the base. Each surgical sponge has a signal receiver and a sound emitter in operational communication with the signal receiver. An antenna is coupled to the base and is in wireless communication with the signal receiver of each surgical sponge. A plurality of batteries is coupled within the base. A battery activator is coupled within the base. The battery activator selectively interrupts or allows operational communication between the plurality of batteries and the antenna. A sound activation lever is coupled to the housing portion and is in operational communication with the antenna.

9 Claims, 6 Drawing Sheets

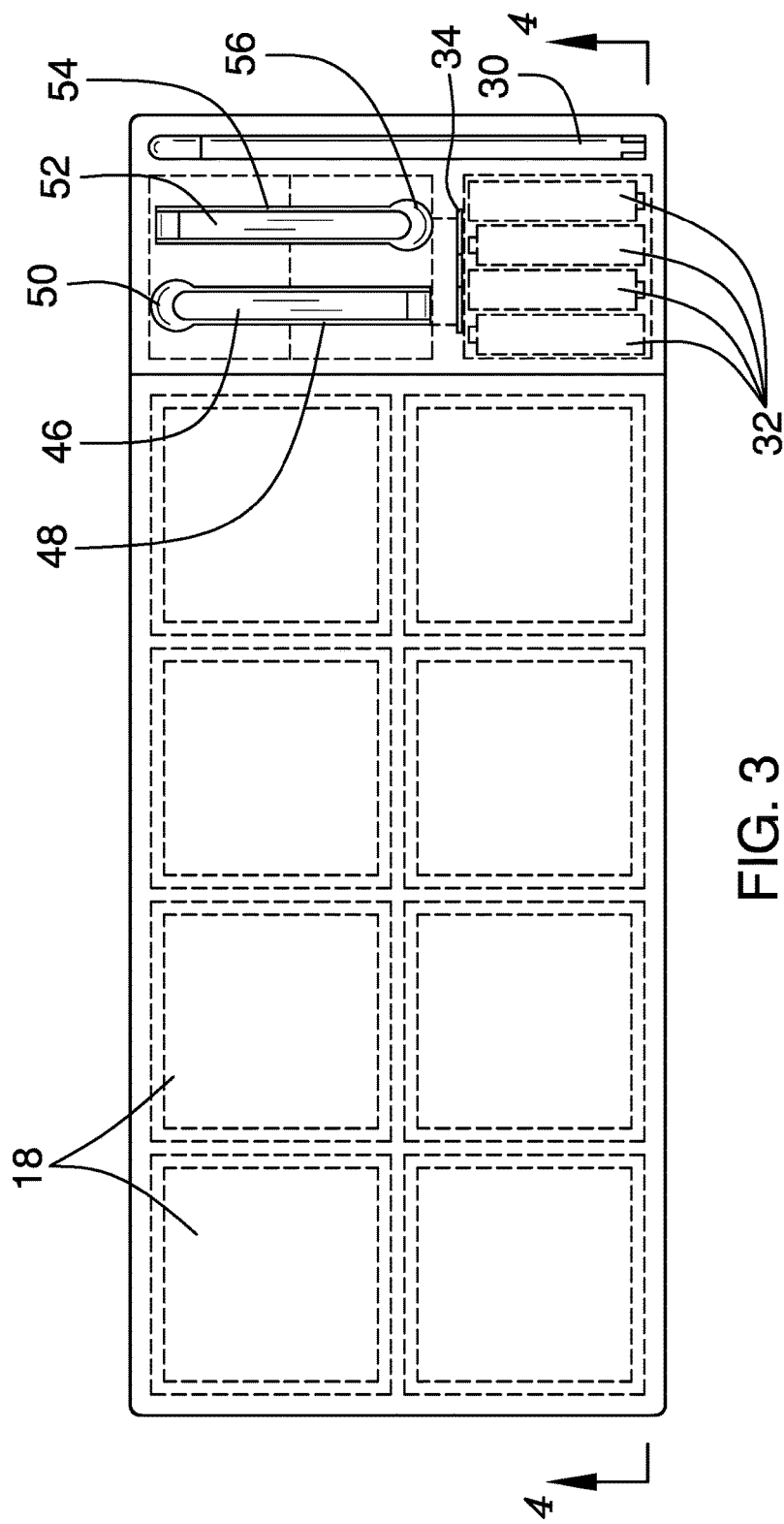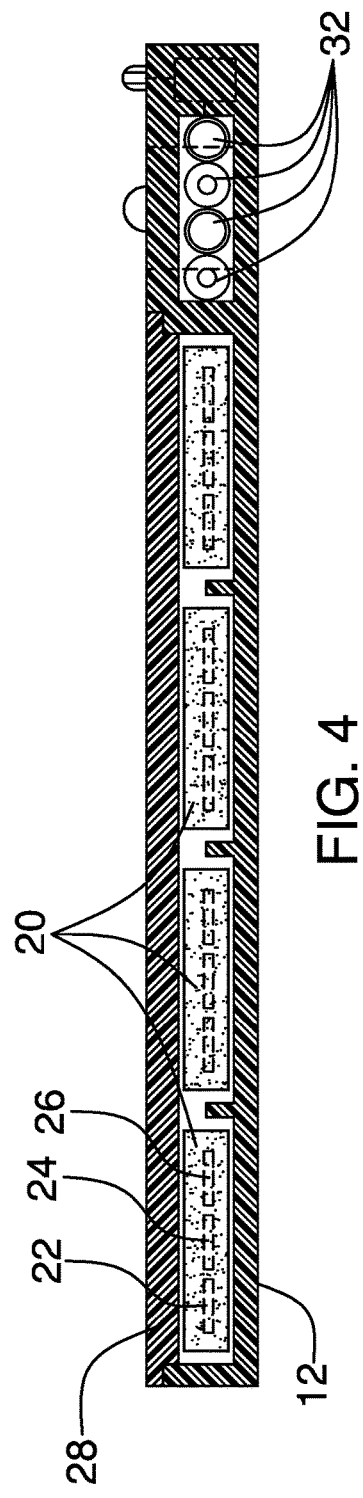

SURGICAL SPONGE LOCATOR SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to surgical devices and more particularly pertains to a new surgical device for locating sponges after surgery for removal.

(2) Description of Related Art Including Information Disclosed Under 37 CFR 1.97 and 1.98

The prior art relates to surgical devices. Known devices attempt to prevent surgical instruments from being left in the patient in a variety of manners. Some devices use metal detection while others use pulse generators or electric markers. These devices do not incorporate a base station for sponges which utilize an FM frequency broadcast to activate either a sound or a light for location.

BRIEF SUMMARY OF THE INVENTION

An embodiment of the disclosure meets the needs presented above by generally comprising a base having a sponge portion and a housing portion. A plurality of surgical sponges is coupled within the base. Each surgical sponge is selectively engageable with the sponge portion. Each surgical sponge has a signal receiver and a sound emitter in operational communication with the signal receiver. An antenna is coupled to the base. The antenna is in wireless communication with the signal receiver of each surgical sponge. A plurality of batteries is coupled within the base. The plurality of batteries is coupled within the housing portion and is in operational communication with the antenna. A battery activator is coupled within the base. The battery activator selectively interrupts or allows operational communication between the plurality of batteries and the antenna. A microprocessor is coupled to the base. The microprocessor is coupled within the housing portion and is in operational communication with the antenna. A sound activation lever is coupled to the base. The sound activation lever is coupled to the housing portion and is in operational communication with the antenna.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 3 is a top plan view of an embodiment of the disclosure.

FIG. 4 is a cross-sectional view of an embodiment of the disclosure along the line 4-4 of FIG. 3.

DETAILED DESCRIPTION OF THE INVENTION

Figure 1:
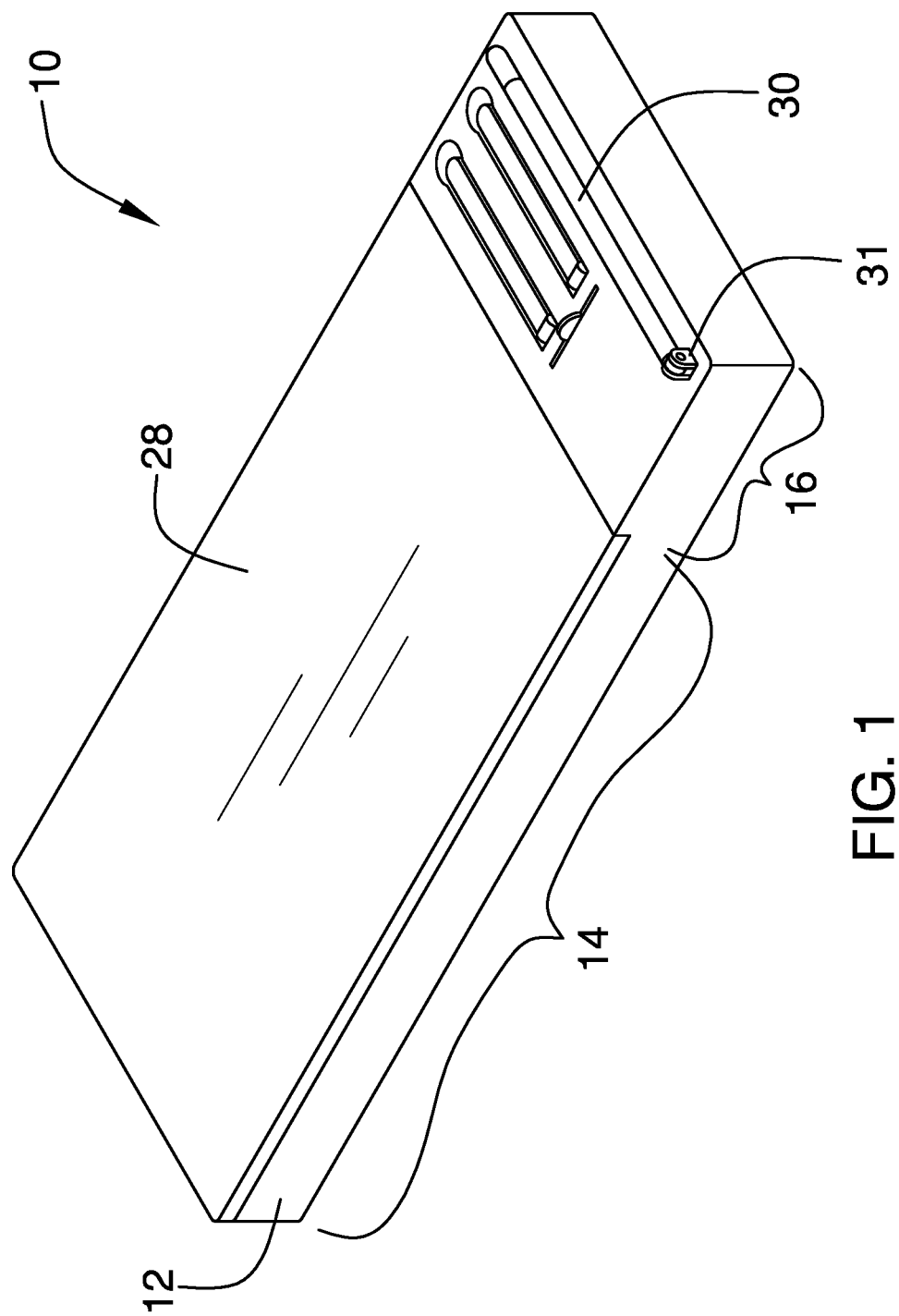
FIG. 1 is an isometric view of a surgical sponge locator system according to an embodiment of the disclosure.
Figure 2:
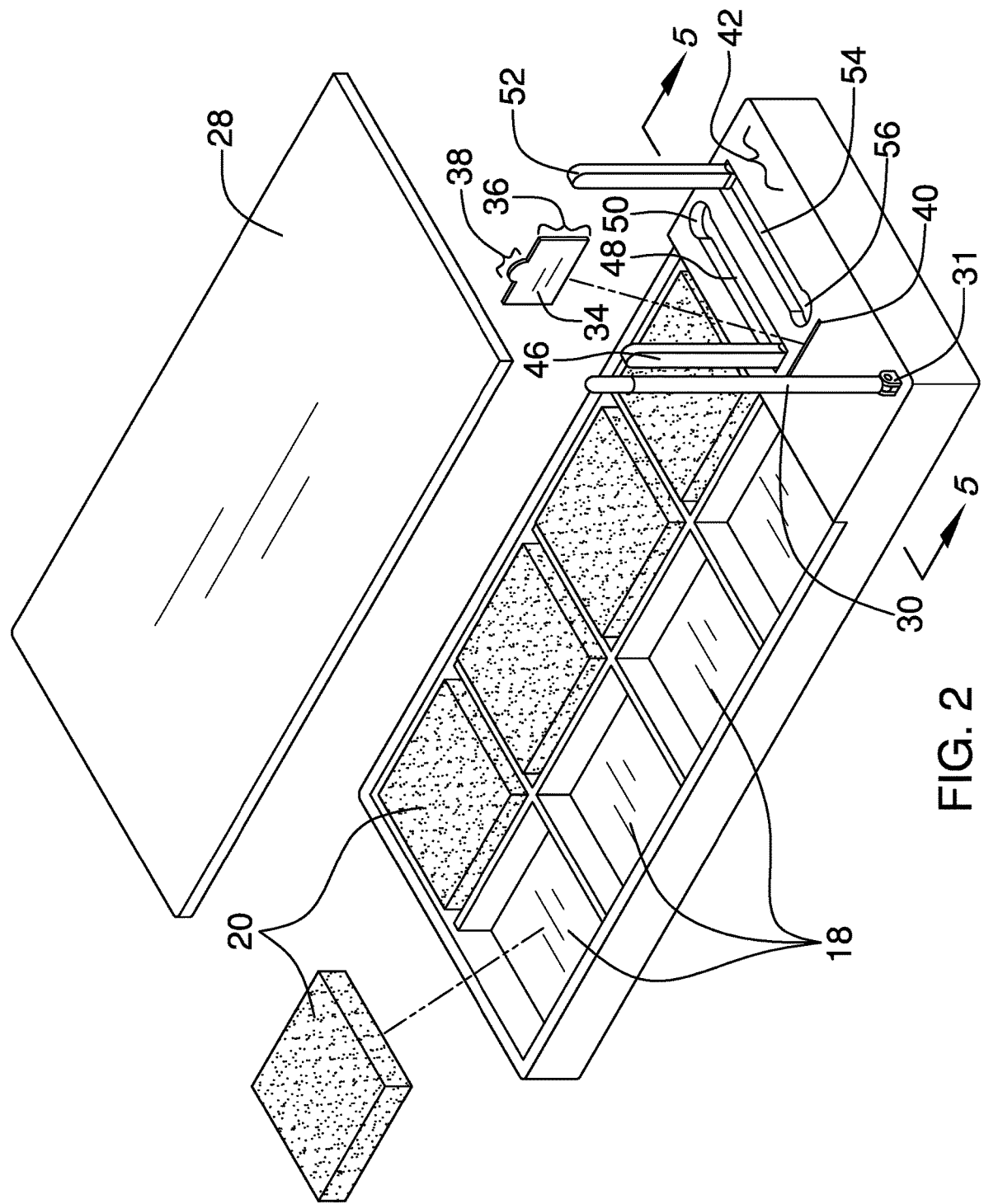
FIG. 2 is an isometric exploded view of an embodiment of the disclosure.
Figure 5:
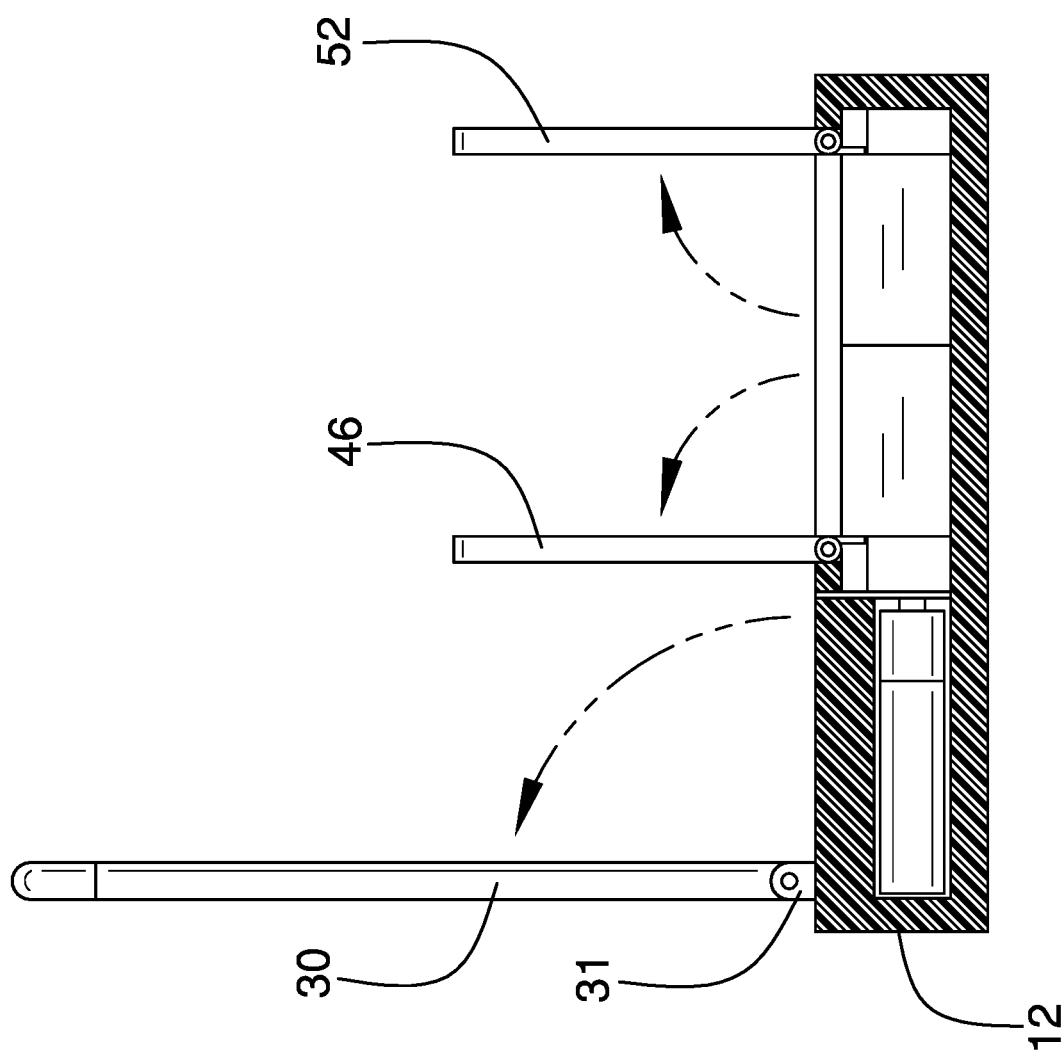
FIG. 5 is a cross-sectional view of an embodiment of the disclosure along the line 5-5 of FIG. 2.
Figure 6:
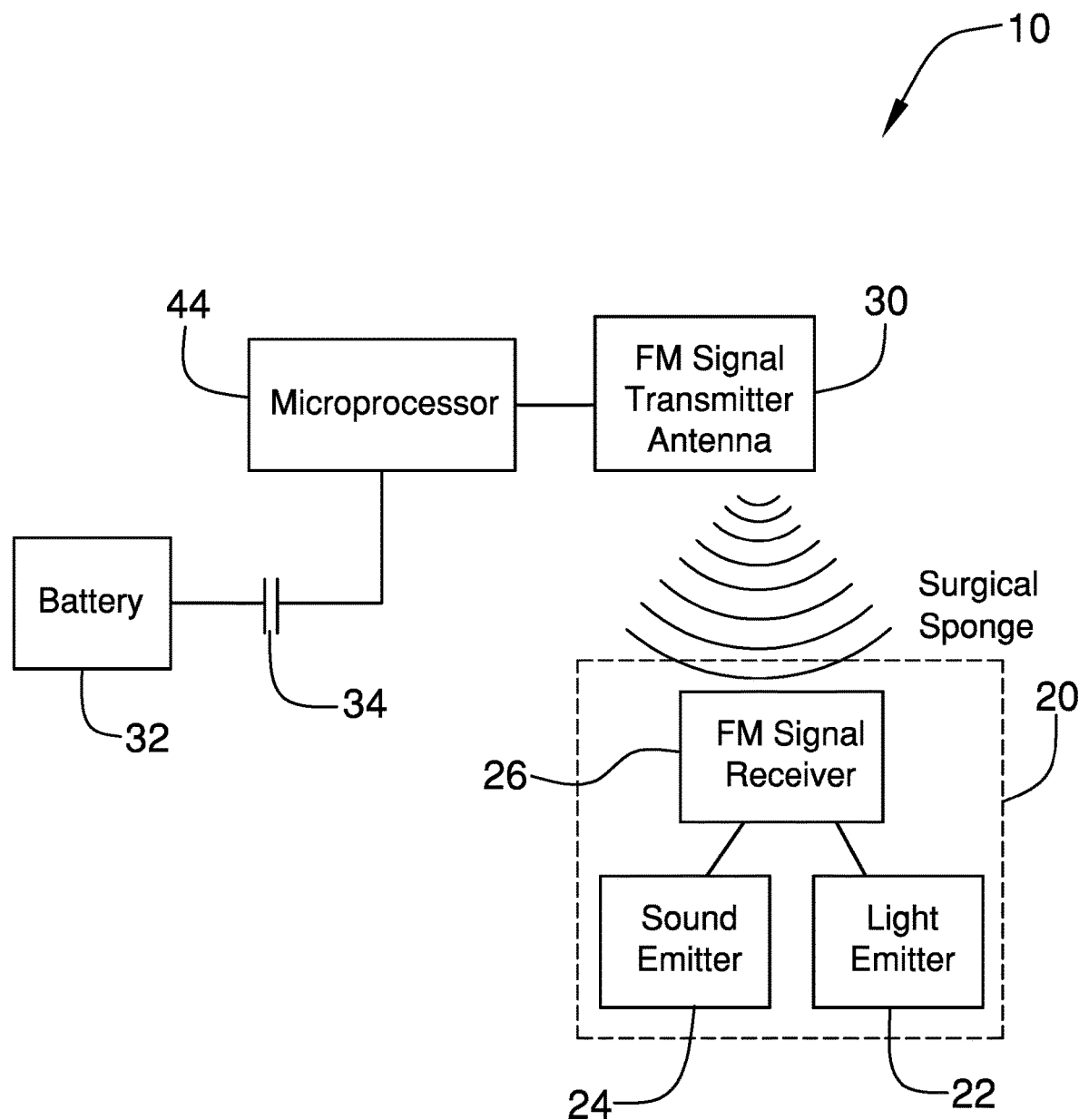
FIG. 6 is a block diagram of an embodiment of the disclosure.
Figure 7:
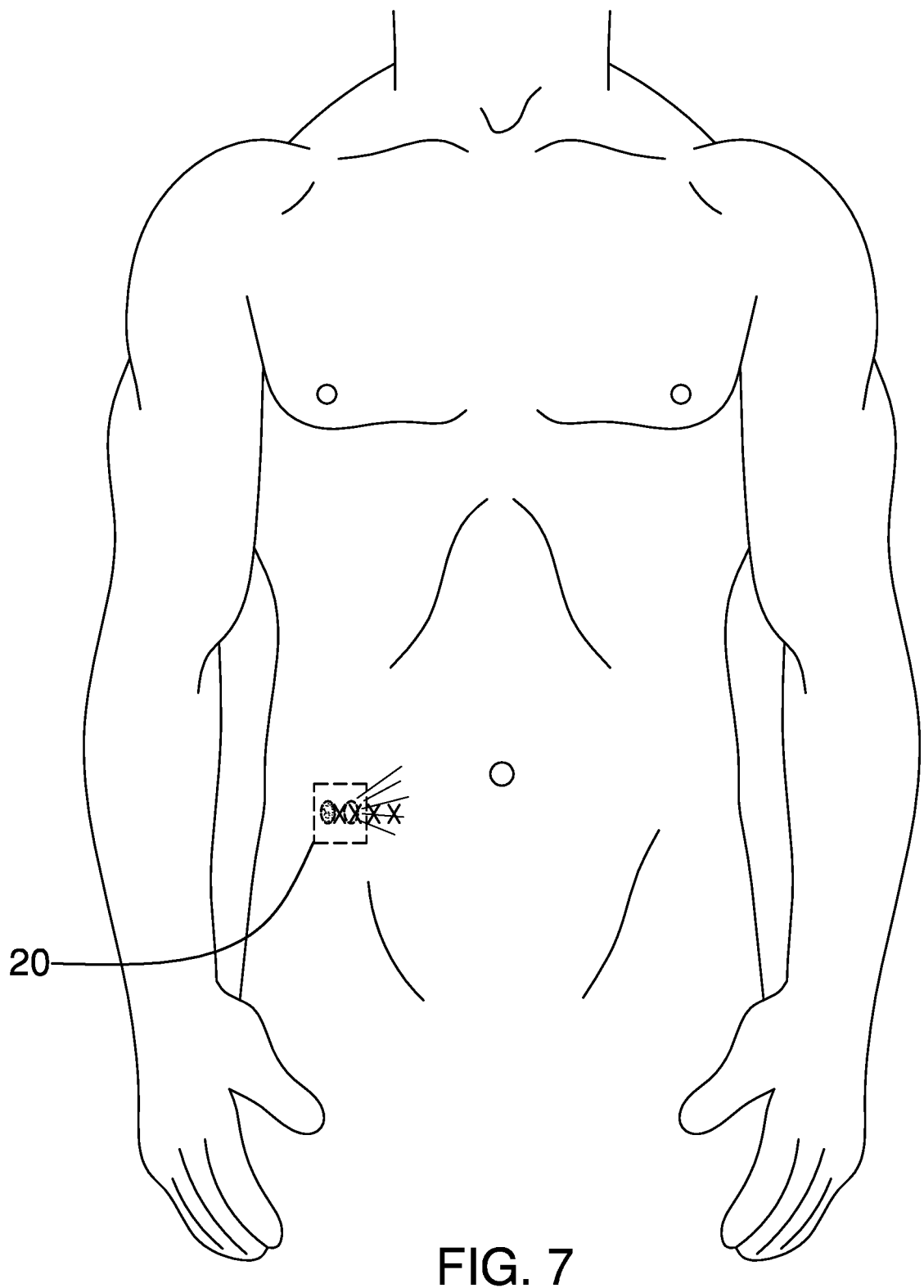
FIG. 7 is an in-use view of an embodiment of the disclosure.

With reference now to the drawings, and in particular to FIGS. 1 through 7 thereof, a new surgical device embodying the principles and concepts of an embodiment of the disclosure and generally designated by the reference numeral 10 will be described.

As best illustrated in FIGS. 1 through 7, the surgical sponge locator system 10 generally comprises a base 12 having a sponge portion 14 and a housing portion 16. The sponge portion 14 of the base has a plurality of sponge recessions 18. A plurality of surgical sponges 20 is coupled within the base 12. Each of the plurality of surgical sponges 20 is selectively engageable within the plurality of sponge recessions 18. Each surgical sponge 20 has a light emitter 22 and a sound emitter 24 in operational communication with a signal receiver 26.

A lid 28 is rectangular and selectively engageable with the base 12 to cover the sponge portion 14. An antenna 30 is coupled to the base 12. The antenna 30 is hingingly coupled to the housing portion 16 of the base. The antenna 30 may have a pair of hinge ears 31 coupled to the housing portion 16. The antenna 30 is in wireless communication with the signal receiver 26 of each surgical sponge.

A plurality of batteries 32 is coupled within the base 12. The plurality of batteries 32 is coupled within the housing portion 16 and is in operational communication with the antenna 30. A battery activator 34 is coupled within the base 12. The battery activator 34 may have a rectangular tab portion 36 and a semicircular grip portion 38. The tab portion 36 is selectively engageable within a tab slot 40 extending through a housing top side 42 of the housing portion. The battery activator 34 selectively interrupts or allows operational communication between the plurality of batteries 32 and the antenna 30.

A microprocessor 44 is coupled to the base 12. The microprocessor 44 is coupled within the housing portion 16 and is in operational communication with the antenna 30. A light activation lever 46 is coupled to the base 12. The light activation lever 46 is coupled to the housing portion 16 and is in operational communication with the antenna 30. The light activation lever 46 is pivotably coupled within a light activator depression 48 of the housing top side of the housing portion. The light activation lever 46 moves from a disactivated light position flush within the light activator depression 48 and an activated light position extending perpendicularly from the housing top side 42. The light activator depression 48 may have a round light head portion 50 to allow easier manipulation.

A sound activation lever 52 is coupled to the base 12. The sound activation lever 52 is coupled to the housing portion 16 and is in operational communication with the antenna 30. The sound activation lever 52 is pivotably coupled within a sound activator depression 54 of the housing top side of the housing portion. The sound activation lever 52 moves from a disactivated sound position flush within the sound activator depression 54 and an activated sound position extending perpendicularly from the housing top side 42. The sound activator depression 54 may have a round sound head portion 56 to allow easier manipulation.

In use, once a surgery is complete the user pulls the battery activator 34 to give power to the antenna 30. The user then lifts the light activation lever 46 to make the light emitter 22 of each surgical sponge emit light to help with visibility. The user may also lift the sound activation lever 52 to make the sound emitter 24 of each surgical sponge emit a sound to help locate when not visible.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A surgical sponge locator system comprising:
   a base, the base having a sponge portion and a housing portion;
   a plurality of surgical sponges coupled within the base, each surgical sponge being selectively engageable with the sponge portion, each surgical sponge having a signal receiver and a sound emitter in operational communication with the signal receiver;
   an antenna coupled to the base, the antenna being in wireless communication with the signal receiver of each surgical sponge;
   a plurality of batteries coupled within the base, the plurality of batteries being coupled within the housing portion and being in operational communication with the antenna;
   a battery activator coupled within the base, the battery activator selectively interrupting or allowing operational communication between the plurality of batteries and the antenna;
   a microprocessor coupled to the base, the microprocessor being coupled within the housing portion and being in operational communication with the antenna; and
   a sound activation lever coupled to the base, the sound activation lever being coupled to the housing portion and being in operational communication with the antenna.

2. The surgical sponge locator system of claim 1 further comprising each surgical sponge having a light emitter in operational communication with the signal receiver; a light activation lever coupled to the base, the light activation lever being coupled to the housing portion and being in operational communication with the antenna.

3. The surgical sponge locator system of claim 2 further comprising the light activation lever being pivotably coupled within a light activator depression of a housing top side of the housing portion, the light activation lever moving from a disactivated light position flush within the light activator depression and an activated light position extending perpendicularly from the housing top side, the light activator depression having a round light head portion to allow easier manipulation.

4. The surgical sponge locator system of claim 1 further comprising the sound activation lever being pivotably coupled within a sound activator depression of a housing top side of the housing portion, the sound activation lever moving from a disactivated sound position flush within the sound activator depression and an activated sound position extending perpendicularly from the housing top side, the sound activator depression having a round sound head portion to allow easier manipulation.

5. The surgical sponge locator system of claim 1 further comprising the antenna being hingingly coupled to the housing portion of the base.

6. The surgical sponge locator system of claim 1 further comprising the sponge portion of the base having a plurality of sponge recessions, each of the plurality of surgical sponges being selectively engageable within the plurality of sponge recessions.

7. The surgical sponge locator system of claim 1 further comprising a lid, the lid being rectangular and selectively engageable with the base to cover the sponge portion.

8. The surgical sponge locator system of claim 1 further comprising the battery activator having a rectangular tab portion and a semicircular grip portion, the tab portion being selectively engageable within a tab slot extending through a housing top side of the housing portion.

9. A surgical sponge locator system comprising:

a base, the base having a sponge portion and a housing portion, the sponge portion of the base having a plurality of sponge recessions;

a plurality of surgical sponges coupled within the base, each of the plurality of surgical sponges being selectively engageable within the plurality of sponge recessions, each surgical sponge having a light emitter and a sound emitter in operational communication with a signal receiver;

a lid, the lid being rectangular and selectively engageable with the base to cover the sponge portion;

an antenna coupled to the base, the antenna being hingingly coupled to the housing portion of the base, the antenna being in wireless communication with the signal receiver of each surgical sponge;

a plurality of batteries coupled within the base, the plurality of batteries being coupled within the housing portion and being in operational communication with the antenna;

a battery activator coupled within the base, the battery activator having a rectangular tab portion and a semicircular grip portion, the tab portion being selectively engageable within a tab slot extending through a housing top side of the housing portion, the battery activator selectively interrupting or allowing operational communication between the plurality of batteries and the antenna;

a microprocessor coupled to the base, the microprocessor being coupled within the housing portion and being in operational communication with the antenna;

a light activation lever coupled to the base, the light activation lever being coupled to the housing portion and being in operational communication with the antenna, the light activation lever being pivotably coupled within a light activator depression of the housing top side of the housing portion, the light activation lever moving from a disactivated light position flush within the light activator depression and an activated light position extending perpendicularly from the housing top side, the light activator depression having a round light head portion to allow easier manipulation; and a sound activation lever coupled to the base, the sound activation lever being coupled to the housing portion and being in operational communication with the antenna, the sound activation lever being pivotably coupled within a sound activator depression of the housing top side of the housing portion, the sound activation lever moving from a disactivated sound position flush within the sound activator depression and an activated sound position extending perpendicularly from the housing top side, the sound activator depression having a round sound head portion to allow easier manipulation.

\* \* \* \* \*